United States Patent
Perricone

(10) Patent No.: US 8,986,739 B2
(45) Date of Patent: Mar. 24, 2015

(54) TREATMENT OF URINARY INCONTINENCE USING NITRONE SPIN TRAPS

(76) Inventor: Nicholas V. Perricone, Meriden, CT (US)

(*) Notice: Subject to any disclaimer, the term of this patent is extended or adjusted under 35 U.S.C. 154(b) by 459 days.

(21) Appl. No.: 13/037,024

(22) Filed: Feb. 28, 2011

(65) Prior Publication Data

US 2012/0219630 A1 Aug. 30, 2012

(51) Int. Cl.
| | |
|---|---|
| A61K 9/14 | (2006.01) |
| A61K 31/685 | (2006.01) |
| A61K 31/15 | (2006.01) |
| A61K 31/20 | (2006.01) |
| A61K 31/23 | (2006.01) |

(52) U.S. Cl.
CPC ............... *A61K 31/685* (2013.01); *A61K 31/15* (2013.01); *A61K 31/20* (2013.01); *A61K 31/23* (2013.01)
USPC ........................................................ 424/489

(58) Field of Classification Search
None
See application file for complete search history.

(56) References Cited

U.S. PATENT DOCUMENTS

| | | | |
|---|---|---|---|
| 5,405,874 A | 4/1995 | Carney et al. | |
| 5,505,962 A | 4/1996 | Sparks | |
| 5,637,320 A | 6/1997 | Bourke et al. | |
| 5,641,515 A | 6/1997 | Ramtoola | |
| 5,681,845 A | 10/1997 | Janzen et al. | |
| 5,681,965 A | 10/1997 | Carney et al. | |
| 6,002,001 A | 12/1999 | Carney et al. | |
| RE36,594 E | 2/2000 | Janzen et al. | |
| 6,376,540 B1 | 4/2002 | Kelleher et al. | |
| 6,717,012 B2 * | 4/2004 | Wang et al. | 564/299 |
| 6,797,459 B2 | 9/2004 | Shirata | |
| 6,852,889 B2 | 2/2005 | Wang et al. | |
| 7,118,762 B2 * | 10/2006 | Byrd | 424/468 |
| 7,338,667 B2 | 3/2008 | Norden et al. | |
| 7,572,462 B2 | 8/2009 | Lane | |
| 2004/0265345 A1 * | 12/2004 | Perricone | 424/401 |
| 2005/0059638 A1 * | 3/2005 | Kelly et al. | 514/114 |
| 2005/0192281 A1 * | 9/2005 | Kelly et al. | 514/248 |
| 2005/0272724 A1 * | 12/2005 | Carney et al. | 514/226.2 |
| 2006/0127469 A1 * | 6/2006 | Perricone et al. | 424/450 |
| 2007/0196396 A1 | 8/2007 | Pilgaonkar et al. | |
| 2008/0167474 A1 | 7/2008 | Becker et al. | |
| 2009/0318454 A1 | 12/2009 | Weiner et al. | |

OTHER PUBLICATIONS

Drugs, Jul. 2004, vol. 64, Issue 14, pp. 1503-1516 Pharmacotherapy for Stress Urinary Incontinence.*
Latini et al. (Adult Urology, Urology 67 (3), 2006, 550-554, 2006 Efficacy of Sacral Neuromodulation for Symptomatic Treatment of Refractory Urinary Urge Incontinence Jerilyn M. Latini, Mohammad Alipour, and Karl J. Kreder, Jr).*
International Search Report & Written Opinion of the international Searching Authority; Application No. PCT/US2012/026929; Completed: May 30, 2012; Mailed: Jun. 12, 2012; 8 pages.
Levin, et al.; "Oxidative Stress and Lower Urinary Tract Dysfunctions Primarily Found in Women"; Urol Sci 2010; 21 (1) pp. 8-18.
European Search Report Application No. EP 12 75 1765 Completed: Sep. 25, 2014; Mailing Date: Oct. 10, 2014 6 pages.

* cited by examiner

*Primary Examiner* — Snigdha Maewall
(74) *Attorney, Agent, or Firm* — St. Onge Steward Johnston & Reens LLC

(57) ABSTRACT

Urinary incontinence is treated by administration of pharmaceutical compositions containing at least one nitrone spin trap such as α-phenyl t-butyl nitrone (PBN) and derivatives thereof. Preferred compositions and methods of treatment further comprise at least one adjunctive ingredient including fatty acid esters of ascorbic acid such as ascorbyl palmitate and ascorbyl stearate, and polyenylphosphatidylcholine.

26 Claims, No Drawings

TREATMENT OF URINARY INCONTINENCE USING NITRONE SPIN TRAPS

FIELD OF THE INVENTION

The present invention relates to pharmaceutical compositions comprising at least one nitrone spin trap and methods of use thereof for the prevention and treatment of urinary incontinence.

BACKGROUND OF THE INVENTION

Urinary incontinence is defined by the International Continence Society as the objective demonstration of involuntary loss of urine. Over 13 million American men and women suffer from urinary incontinence. Urinary incontinence causes many social and economic problems, such as loss of self-esteem, embarrassment, restriction of social and sexual activities, isolation, and dependence on caregivers. Urinary incontinence may also lead to many medical complications, for example, skin rashes, the lower urinary tract inflammation, and bladder and kidney infections.

There are five basic types of urinary incontinence based on the pattern of symptoms: (1) stress incontinence, which is involuntary loss of urine during coughing, sneezing, laughing, or other physical activity; (2) urge incontinence, which is involuntary loss of urine associated with an abrupt or strong desire to void; (3) overflow incontinence, which is involuntary loss of urine associated with over-distension of the bladder; (4) mixed incontinence, which is a combination of at least two of the above types; and (5) functional incontinence, which refers to urine loss resulting from the inability to get to a toilet. Among these types, stress incontinence and urge incontinence are two major types. The underlying pathology of stress incontinence involves the dysfunction of rhabdosphincter which is responsible for contraction of the urethral smooth muscle and of the external striated sphincter to ensure the closure of the bladder during the urine filling phase. The underlying pathology of urge incontinence involves disturbance in bladder functions as a result of unrestricted contractions of the detrusor muscle. Chutka, D. S. and Takahashi P. Y., *Drugs* 560: 587-595 (1998).

Urinary incontinence can have many etiologies, some are transient (transient incontinence) while others are of a more permanent nature (established incontinence). Transient incontinence is most often caused by bladder or lower urine tract infections. Established incontinence may be caused by brain and spinal cord disorders such as stroke, Alzheimer's disease, and multiple sclerosis; diseases that affect the nerves leading to and from the bladder such as diabetes; conditions in the lower urinary tract such as an enlarged prostate; and conditions that permanently impair mental function or mobility.

Under normal conditions, the lower urinary tract functions through a system of highly coordinated processes that involve the control of smooth and skeletal muscles of the bladder and urethra, by both central and peripheral nervous systems. Therefore, urinary incontinence is also regarded as a neuromuscular disorder when dysfunctional muscles of the bladder and urethra are caused by damaged nerve systems. Like most other neuromuscular disorders, such damages often arise from or are characterized by oxidative damages or stress. Recent studies reported the link between oxidative stress/increased free-radicals and urinary incontinence. Levin, R. M., et al. *Oxidative Stress and Lower Urinary Tract Dysfunctions Primarily Found in Women*, Urological Science, 21, 8-18 (2010); Kurutas E. B., et al. *The Effects of Oxidative Stress in Urinary Tract Infection, Mediators of Inflammation*, 4, 242-244 (2005).

Treatment options for urinary incontinence range from more conservative approaches, including behavioral techniques and physical therapy to more aggressive options, such as surgery. For most patients suffering minor to moderate urinary incontinence symptoms, medications, optionally in conjunction with behavioral techniques, are preferred treatment. Current medications focus on treating urinary incontinence with substances that act on the reflexes of the lower urinary tract. These medications include parasympatholytics such as oxybutynin (Ditropan), tolterodine (Detrol), darifenacin (Enablex), solifenacin (Vesicare) or trospium (Sanctura), tricyclic antidepressants such as imipramine (Tofranil), or muscle relaxants such as flavoxate. Other medications increase the tone of the urethral sphincter such as Duloxetine (Yentreve), and topical creams tone and rejuvenate tissues in the urethra and vaginal areas such as topical estrogen. However, most of them have adverse effects that greatly limit the use thereof. Burgard et al, *New pharmacological treatments for urinary incontinence and overactive bladder*, Curr. Opin. Investig. Drugs. 6, 81-89 (2005); Ouslander J. G. *Management of Overactive Bladder*, N. Engl. J. Med. 350:786-99 (2004).

There is a clear need for new, well-tolerated therapies that effectively treat urinary incontinence and achieve the greatest possible long-term improvement in patients affected by urinary incontinence, either as monotherapy or in combination with available therapies.

As set forth in more detail hereafter, the present invention is based on pharmaceutical compositions comprising at least one nitrone spin trap for the prevention and treatment of urinary incontinence and other lower urinary tract dysfunctions.

Nitrone spin traps are potent free radical scavengers and are commonly used as research aids or diagnostic tools to detect free radicals. Sudha Rana, *Electron paramagnetic resonance spectroscopy in radiation research: Current status and perspectives*, J. Pharmacy & BioAllied Sciences, 2, 80-87 (2010). Nitrone spin traps have strong antioxidant capabilities and have been suggested for various therapeutic uses. For example, PBN and derivatives thereof have been reported for treating a wide variety of disease conditions arising from or characterized by free radical-induced oxidative damages. Such disease conditions include, for example, disorders of the central and peripheral nervous systems, such as stroke, Parkinsonism, traumatic nerve damage and the like, and disorders of the peripheral organs, such as atherosclerosis, cardiac infarction, ulcerative colitis and the like. Nitrone spin traps have also been reported to treat certain inflammatory conditions, such as asthma and arthritis.

It would be desirable to have an effective treatment for urinary incontinence using nitrone spin traps.

SUMMARY OF THE INVENTION

The object of this invention is to provide prevention and treatment methods for urinary incontinence, and more particularly, to provide an effective therapeutic agent with little or less side effects, and with less frequent daily administration.

This and other objectives of the invention are accomplished by the present invention, which provides pharmaceutical compositions comprising at least one nitrone spin trap, preferably PBN and derivatives, and a pharmaceutically acceptable carrier, for the treatment and prevention of urinary incontinence.

In order to provide an effective therapeutic agent for treating urinary incontinence, it is desirable to be able to administer the nitrone spin traps at high doses, especially initially. Thus, the nitrone spin traps used to treat incontinence conditions in accordance with the invention are non-toxic or have very low toxicity.

It is also important for the nitrone spin traps to efficiently reach the biological site. Thus, it is particularly desirable to formulate the nitrone spin traps for improved bioavailability and cellular permeability.

Since urinary incontinence can be a long term disease, it is further desirable that the nitrone spin traps are formulated into dosage forms suitable for oral administration no more than three times a day for patients' convenience, tolerance and compliance.

The composition may further comprise at least one adjunct ingredient such as fatty acids, fatty acid esters of ascorbic acid, and polyenylphosphatidylcholine. The amount of each adjunct ingredient is at a range of about 0.025 w/w % to about 0.5 w/w %.

Oral administration is preferred for patient's convenience, tolerance and compliance. The oral carrier can be formulated as an immediate release carrier or various controlled released carriers. The composition suitable for oral administration in an immediate release carrier typically contains from about 1 w/w % to about 30 w/w % of the nitrone spin trap. The composition suitable for oral administration in a controlled release carrier typically contains from about 5 w/w % to about 50 w/w % of the nitrone spin trap. Parenteral administration provides an alternative effective means of administration. A typical parenteral composition contains from about 0.1 w/w % to about 20 w/w % of the nitrone spin trap.

The amount of the nitrone spin trap necessary to bring about the therapeutic treatment of urinary incontinence is not fixed per se, and necessarily is dependent upon the severity and extent of the disease, the form of the nitrone spin trap employed, and the concentration of the nitrone spin trap in the pharmaceutical composition. A typical daily dosage ranges from about 0.1 mg/kg/day to about 100 mg/kg/day, preferably from about 10 mg/kg/day to about 60 mg/kg/day, and more preferably from about 15 mg/kg/day to about 45 mg/kg/day. The composition may be administered at predetermined intervals, ranges from one to three times a day, preferably once a day.

DETAILED DESCRIPTION OF THE INVENTION

The present invention provides methods of prevention and treatment of urinary incontinence by treating a patient in need with pharmaceutical compositions comprising an effective amount of at least one nitrone spin trap and a pharmaceutically acceptable carrier.

As used herein, the term "nitrone spin trap(s)" used herein and after refers to both nitrone spin traps and derivatives thereof; the term "patient(s)" refers to human beings and animals, including companion animals such as dogs, cats and horses; the term "urinary incontinence" refers to urge incontinence, stress incontinence, and mixed incontinence.

Any nitrone spin traps, either in straight chain or in cyclic configuration, may be employed in compositions of the invention. Common nitrone spin traps can typically be purchased from Sigma-Aldrich Chemical Co. or other chemical vendors. Uncommon nitrone spin traps, for example, azulenyl nitrone spin traps and furan nitrone spin traps, can be synthesized following the procedures known in the art. U.S. Pat. No. 6,376,540 to Kelleher and U.S. Pat. App. No. 20080167474 to Becker have reported the synthesis of these types of nitrone spin traps, the disclosure of which is incorporated by references in entirety. Regardless the source of the spin traps, it is important that the spin traps are sufficiently pure and sterile to meet the standards set by the United States Pharmacopeia. Any impurities should be inert in the sense of not bringing about deactivation of the nitrone spin traps. Preferred nitrone spin traps should have minimal or no toxicity to normal cells. Suitable nitrone spin traps include, but is not limited to, phenyl N-tert-butylnitrone, also referred to as α-phenyl t-butyl nitrone (PBN), 5,5-dimethyl pyrroline N-oxide (DMPO), α-(4-pyridyl 1-oxide)-N-tert-butylnitrone (POBN), 3,3,5,5-tetramethyl-l-pyrroline N-oxide, and 2,4,4,6-tri-tert-butylnitrosobenzene (BNB). Other nitrone spin traps described in U.S. Pat. Nos. 5,405,874, 5,681,845, 5,681, 965, 6,002,001 and RE. 36,594 can also be used, the disclosure of which is incorporated herein by reference.

The most preferred nitrone spin traps are PBN and derivatives thereof, because they have no measurable effect on normal or uninjured cells. PBN and derivatives thereof have the following general formula:

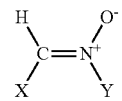

wherein X is phenyl or substituted phenyl with up to five substitutions on the phenyl ring, and each substitution is independently (can vary within the molecule) selected from the group consisting of hydrogen, halogen, alkyl, substituted alkyl, alkaryl, alkoxyl, alkenyl, and amino; and Y is selected from the group consisting of alkyl, substituted alkyl, alkenyl, alkynyl, naphthyl, heterocyclic, alkcycloalkyl, cycloalkyl and cycloalkenyl.

"Alkyl" refers to monovalent alkyl groups preferably having from 1 to about 12 carbon atoms, more preferably 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like.

"Amino" refers to primary, secondary and tertiary alkyl substituted amino groups and the like.

"Substituted alkyl" refers to an alkyl group preferably having from 1 to about 12 carbon atoms, more preferably 1 to 8 carbon atoms and still more preferably 1 to 6 carbon atoms, which is substituted with from 1 to 3 substituents selected from the group consisting of alkoxy, amino, mono- and dialkylamino, aminoacyl, aminocarbonyl, alkoxycarbonyl, aryl, carboxyl, cyano, halo, heterocyclic, hydroxy, nitro, thioalkoxy and the like. A preferred substituted alkyl group is the trifluoromethyl group.

"Alkaryl" refers to alkylene-aryl groups preferably having from 1 to 10 carbon atoms in the alkylene moiety and from 6 to 14 carbon atoms in the aryl moiety. Such alkaryl groups are exemplified by benzyl, phenethyl, and the like.

"Alkcycloalkyl" refers to alkylene-cycloalkyl groups preferably having from 1 to 10 carbon atoms in the alkylene moiety and from 3 to 8 carbon atoms in the cycloalkyl moiety. Such alkcycloalkyl groups are exemplified by cyclopropyl, cyclopentyl, cyclohexyl, and the like.

"Alkoxy" refers to the group "alkyl-O—". Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkenyl" refers to alkenyl groups preferably having from 2 to 10 carbon atoms and more preferably 2 to 6 carbon atoms and having at least 1 and preferably from 1-2 sites of alkenyl unsaturation. Preferred alkenyl groups include ethenyl, n-propenyl, isopropenyl, and the like.

"Alkynyl" refers to alkynyl groups preferably having from 2 to 10 carbon atoms and more preferably 2 to 6 carbon atoms and having at least 1 and preferably from 1-2 sites of alkynyl unsaturation. Preferred alkynyl groups include ethynyl, propargyl, and the like.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Halo" or "halogen" refers to fluoro, chloro, bromo and iodo. Preferred halo groups are either fluoro or chloro.

"Heterocycle" or "heterocyclic" refers to a monovalent saturated or unsaturated group having a single ring or multiple condensed rings, from 1 to 10 carbon atoms and from 1 to 4 hetero atoms selected from nitrogen, sulfur or oxygen within the ring. Examples of heterocycles include, but are not limited to, morpholine, piperazine, imidazolidine, pyrrolidine, piperidine and the like.

"Naphthyl" refers to naphthyl ring and can optionally be substituted with from 1 to 3 substituents selected from the group consisting of alkyl, substituted alkyl, alkoxy, alkenyl, alkynyl, amino, aminoacyl, aminocarbonyl, alkoxycarbonyl, aryl, carboxyl, cyano, halo, hydroxy, nitro, trihalomethyl and the like.

The quantity of the nitrone spin trap in the composition is not fixed per se and will be set in details in the sections regarding the carriers.

Some embodiments of this invention contain at least one other adjunct ingredient in addition to the nitrone spin trap. Adjunct ingredients include, but are not limited to, fatty acids, which may be in the form of fatty acid esters, and polyenylphosphatidylcholine. Since PBN degrades at pH less than approximately 3 to 4, it is important that the amount of the fatty acid or other ingredients added would not bring the composition to a pH below 4. Many embodiments employ more than one adjunct ingredient at a range from about 0.025 w/w % to about 0.5 w/w % of each of the adjunct ingredient.

As used herein, the term "fatty acid" has reference to and encompasses all isomers of the free acid and structurally related, biologically equivalent derivatives such as salts and esters. Suitable fatty acids include, but not limited to, long chain fatty acids such as lipoic acid and ascorbic acid, essential fatty acids such as omega-3 fatty acid, linoleic acid, and omega-6 fatty acid, and arachidonic acid.

The most preferred fatty acid is ascorbic acid (vitamin C), which is often employed in the form of fat-soluble fatty acid esters of ascorbic acid. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly ascorbyl stearate, are included. The esters may be prepared using hydrogenated oils or fats, or fractions thereof, and contain small amounts of another ester. Ascorbyl stearate prepared using canola, for example, commonly contain about 4% ascorbyl palmitate. It is an advantage of the invention to employ fatty acid esters of ascorbic acid because they help stabilize and solubilize the nitrone spin trap in the composition.

Polyenylphosphatidylcholine (PPC) is employed as an adjunct ingredient in other embodiments, alone or in combination with the fatty acids. By "polyenylphosphatidylcholine" it meant any phosphatidylcholine (PC) bearing two fatty acid substituents, wherein at least one is an unsaturated fatty acid with at least two double bonds. Preferred polyenylphosphatidylcholines contain at least one linoleic (18:2) group, most preferably two, in a cis geometrical configuration typical of natural products, which presents in the preparation at levels of at least about 25%, preferably at least about 40% by weight. Other forms of PPC can also be used as those set out in U.S. Pat. No. 6,797,459 at column 3 lines 34 to 52. PPC itself is an active antioxidant that has been shown to protect against lipid peroxidation and liver damage, including fibrosis and cirrhosis (Aleynik, S. I., et al., *J. Investig. Med.* 47: 507-512 (1999)). Moreover, because PC itself is a major constituent of cell membranes, PPC greatly enhances the antioxidant activity of the composition because it facilitates the nitrone spin traps to penetrate and disperse in cell membranes in quantities sufficient to reach therapeutic levels.

Suitable carriers should be those in which nitrone spin traps are soluble per se or effectively solubilized. Where employed, the carriers should be inert in the sense of not bringing about deactivation or oxidation of the nitrone spin traps. Suitable carriers for the present invention include oral carriers, parenteral carriers, topical carriers, and intranasal carriers. Among them, oral carriers are particularly preferred for patients' convenience, tolerance and compliance.

The oral carriers in accordance with the present invention can be conventional immediate release carriers. The materials as well as processing techniques and the like for conventional immediate release carriers are set forth in *Remington's Pharmaceutical Sciences*, 17$^{th}$ edition, 1985, Mack Publishing Company, Easton, Pa., which are incorporated by reference.

The oral carriers can also be controlled release carriers. Controlled release within the scope of the invention can be taken to mean any one of a number of extended release dosage forms. Preferred controlled release formulations release the active ingredient gradually at a controlled rate of release over 4 hours or more so that a desired level of the nitrone spin traps is maintained in blood serum to provide long term therapeutic effect and to avoid toxicity that may be associated with the spike of the drug concentration of immediate release formulations. Controlled release formulations mean that patients may take the nitrone spin trap in a larger dose at less frequency to reach same therapeutic effect. This feature is particularly beneficial for treating a long term disease such as urinary incontinence. There are corporations with specific expertise in drug delivery technologies including controlled release oral formulations such as Alza Corporation and Elan Corporation. Numerous patents disclose the controlled release oral formulations, such as U.S. Pat. Nos. 5,637,320, 5,505,962, 5,641,515, 7,118,762, 7,338,667, and 7,572,462, the teachings of which are incorporated by references in entirety.

One preferred type of oral controlled release carriers utilizes enteric coatings. Enteric coatings allow the active ingredients to remain physically incorporated in the dosage form for a specific period after oral ingestion and be released from the coatings when the coatings are dissolved in the digestive system at specific pH. The desired pH for the coating dissolution is above pH 5.5 which present in the small intestine. Suitable enteric coating agents include, but not limited to, hydroxypropylmethylcellulose phthalate, methacryclic acid-methacrylic acid ester copolymer, polyvinyl acetate-phthalate and cellulose acetate phthalate.

Another preferred type of oral controlled release carriers employs solid dispersions. Solid dispersions may be defined as dispersions of active ingredients in an inert carrier or matrix in the solid state. Akihiko Hasegawa, *Super Saturation Mechanism of Drugs from Solid Dispersions with Enteric Coating Agents*, Chem. Pharm. Bull. 36: 4941 4950 (1998). Solid dispersions may be used to improve the solubilities and/or dissolution rates of poorly soluble active ingredients such as fatty nitrones. Hiroshi Yuasa, et al., *Application of the Solid Dispersion Method to the Controlled Release Medicine. III. Control of the Release Rate of Slightly Water-Soluble Medicine From Solid Dispersion Granules*, Chem. Pharm. Bull. 41:397 399 (1993).

The inert carrier may have an influence on the dissolution characteristics of the dispersed drug because the dissolution rate of the drug from a surface may be affected by the carrier in the solid dispersion formulation. For example, a water-soluble carrier may result in a fast release of the nitrone spin trap from the matrix, or a poorly soluble or insoluble carrier may lead to a slower release of the nitrone spin trap from the matrix. The solubility of the nitrone spin trap may also be increased owing to some interaction with the carriers. A preferred solid dispersion carrier is phosphatidylcholine due to its amphoteric nature. Makiko Fuji, et al., *Dissolution of Bioavailability of Phenyloin in Solid Dispersion with Phosphatidylcholine*, Chem. Pharm. Bull 36:4908 4913 (1988).

A third preferred type of oral controlled release carriers utilizes multilayer dosage formulations. In one embodiment, the nitrone spin traps are included in a solid dispersion system and then coated with an enteric polymer. In another embodiment, the nitrone spin traps are in double-layers dosage formulation in which the first extragranular layer may be formulated as an immediate release granulate, and the second intragranular layer may be formulated in a controlled manner, incorporating enteric coatings, solid dispersions, or the combinations thereof. This double-layer dosage formulation provides a wide range of desirable effects in that a high dose of the nitrones can be immediately released to accommodate most severe urinary incontinence conditions followed by a low dose of the nitrones for continued treatment and maintenance.

Pharmaceutical compositions suitable for oral administration are prepared by formulating the nitrone spin traps, and adjunct ingredients if any, with the carrier into suitable dosage forms using conventional methods. Optionally one or more auxiliary ingredients selected from buffers, flavors, surfactants, viscosants, lubricants, etc. can also be added in the formulation. Suitable dosage forms of the present invention include, but not limited to, tablets, sublingual tablets, capsules, powders, granules or fine granules, or suspensions in a non-aqueous liquid such as syrups, emulsions that contain prescribed amount of the active ingredient.

The quantity of the nitrone spin trap in the oral carrier may be varied or adjusted widely depending upon the potency of the particular nitrone spin trap, the desired dosage effective amount and the desired concentration. The quantity of the nitrone spin trap is generally high in controlled release dosage forms and low in immediate release dosage forms. In a controlled release embodiment, the quantity of the nitrone spin trap may range between about 5% to about 50% by weight of the composition; while in an immediate release embodiment, the quantity of the nitrone spin trap is typically between about 1% to about 30% by weight of the composition.

Besides oral carriers, parenteral carriers are viable alternatives for the prevention and treatment of urinary incontinence. Parenteral administration generally provides better bioavailability than other means of administration and thus less medication is required to achieve the same efficacy. Parenteral administration is especially preferred for patients under intensive care or are uncooperative. In parenteral compositions, the nitrone spin trap generally ranges from about 0.1 w/w % to about 20 w/w % with the remainder being the sterile saline, phosphate-buffered saline or other parenteral carriers known in the art.

The therapeutic effective amount of the nitrone spin traps may vary with the administration route, the symptom to be treated, and the patient condition. An appropriate dosage for treating urinary incontinence ranges from about 0.1 mg/kg/day to about 100 mg/kg/day, preferably from about 10 mg/kg/day to about 60 mg/kg/day, and more preferably from about 15 mg/kg/day to about 45 mg/kg/day. It is beneficial to administrate the drug to a patient in need, in equally divided portions, at predetermined intervals, ranges from one to three times a day, preferably once a day. It is noticed that patients have better compliance with less frequent daily administration. Therefore for patients who need long term treatment for urinary incontinence, an orally dose of once a day is particularly attractive. Since gradual improvement is generally noticed with each successive application, it is usually contemplated that a relatively high dosage of nitrone spin trap is delivered during treatment and gradually titration down to a low concentration maintenance dosage. In one embodiment, patients may be treated with a high concentration oral dosage first and gradually reduce to a low concentration oral dosage form. In another embodiment, patients may be treated with a parenteral composition first and wind down to a low concentration oral composition.

Nitrone spin traps may be administered alone or in combination with pharmaceutical formulations containing other active ingredients suitable for treating urinary incontinence. In one embodiment, the composition is administrated in combination with topical estrogens, a non-invasive bladder smooth muscle relaxant.

The mechanisms of action of the therapeutic effectiveness of the nitrone spin traps for urinary incontinence are not fully understood at this time. It has been postulated that urinary incontinence may involve abnormalities in free radical generation and lipid peroxidation which damage the nerve system that is responsible for transmitting sensory information between brain and the lower urinary tract and thus lead to involuntarily urine loss. Without wishing to be bound by theory, it is believed that the nitrone spin traps may act via the peripheral or central nervous system to affect the reflex of bladder muscles in a manner to restore normal functioning of the lower urinary tract.

One theory is that PBN and derivatives, as antioxidants, reduce the levels of the free radicals, especially hydroxyl and superoxide radicals that implicate the nerve system, by forming stable complexes with the free radicals, thus repair the oxidative stress damages to the nerve system and result in a normal reflex of urethral and bladder muscles.

Another theory is that PBN and derivatives may serve as Michael acceptor pharmacophores in binding to, and thus inactivating, the transcription factors which contribute to the pathogenesis of urinary incontinence. This mechanism of action is proposed based on the chemical structure of PBN and derivatives in which an active nitrogen atom is adjacent to an oxygen atom, so that the carbon atom next to the nitrogen becomes electron deficient. This allows PBN and derivatives to act as electrophilic Michael acceptors to bind with the cysteine residues on many different enzyme genera and transcription factors. Since the Michael reaction is irreversible, PBN and derivatives thus permanently inhibit the cellular signal transduction pathways that lead to urinary incontinence.

PBN and derivatives should bind to and inactivate NF-kB, a transcription factor which present at a high level in bladder smooth muscles and which up-regulates over one hundred proinflammatory compounds. NF-kB would cause the immediate early genes fos and jun to combine to form AP1, which in turn would promote the production nerve growth factor (NGF) gene. NGF is a common denominator for human and animal data for urinary incontinence. In animals, a blockade of NGF prevents overactive bladder. Steers, W. *Potential Targets in the Treatment of Urinary Incontinence*, Rev. Urol. 3 (1): S19-26 (2001). Therefore, by inactivating NF-kB, PBN and derivatives should inhibit the primary cellular signal transduction pathways that lead to urinary incontinence and therefore provide for prevention and treatment of urinary incontinence.

In addition, PBN and derivatives should also activate Nrf2, a transcription factor which up regulates about twenty different cyto protective enzymes, phase 2 proteins and antioxidant enzymes, thus inhibiting free radical production and providing a secondary pathway for prevention and treatment of urinary incontinence.

The above described mechanisms of action mean that relatively small amounts of PBN and derivatives are sufficient for effective prevention and treatment of psoriasis. By inactivating the key transcription factors at an early stage of the pathogenesis pathways, PBN and derivatives block the signal transduction pathways, and prevent the subsequent cascading, catalytic, and up-regulated expression of proinflammatory cytokines and chemokines in the urinary incontinence stage. The high efficacy of PBN and derivatives is a particularly beneficial aspect of the present invention.

Methods and compositions of the present invention are also useful for treating overactive bladder and other lower urinary tract diseases. It is generally the case that treatment also decreases both micturition and nocturnal urination frequencies.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims.

What is claimed is:

1. A method for the treatment of urinary incontinence, comprising administrating to a patient in need a pharmaceutical composition comprising a pharmaceutically acceptable carrier and a therapeutically effective amount of at least one nitrone spin trap having the formula (1):

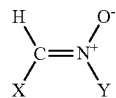

wherein

X is phenyl or substituted phenyl with up to five substitution groups on the phenyl ring, wherein each said substitution groups is independently selected from the group consisting of hydrogen, halogen, alkaryl, alkoxyl, and alkenyl, and Y is selected from the group consisting of alkyl, substituted alkyl, alkenyl, alkynyl, naphthyl, heterocyclic, alkcycloalkyl, and cycloalkenyl.

2. The method according to claim 1, wherein said nitrone spin trap is α-phenyl-tert-butylnitrone.

3. The method according to claim 1, wherein said therapeutically effective amount is 0.1 mg/kg/day to about 100 mg/kg/day.

4. The method according to claim 3, wherein said therapeutically effective amount is from about 10 mg/kg/day to about 60 mg/kg/day.

5. The method according to claim 4, wherein said therapeutically effective amount is about 15 mg/kg/day to about 45 mg/kg/day.

6. The method according to claim 1, wherein said pharmaceutically acceptable carrier is selected from a group consisting of oral carrier, parenteral carrier, topical carrier, and intranasal carrier.

7. The method according to claim 1, wherein said pharmaceutically acceptable carrier is a parenteral carrier and said nitrone spin trap is from about 0.1% to about 20% by weight of the composition.

8. The method according to claim 1, wherein said pharmaceutically acceptable carrier is an oral carrier.

9. The method according to claim 8, wherein said oral carrier is an immediate release drug carrier.

10. The method according to claim 9, wherein said nitrone spin trap is from about 1% to about 30% by weight of the composition.

11. The method according to claim 8, wherein said oral carrier is a controlled release drug carrier.

12. The method according to claim 9, wherein said nitrone spin trap is from about 5% to about 50% by weight of the composition.

13. The method according to claim 11, wherein said controlled release drug carrier is an enteric coating carrier.

14. The method according to claim 11, wherein said controlled release drug carrier is a solid dispersion carrier.

15. The method according to claim 11, wherein said controlled release drug carrier is a double layers dosage carrier in which the first extragranular layer is an immediate release granulate, and the second intragranular layer is a controlled release granulate.

16. The method according to claim 11, wherein said controlled release drug carrier is a solid dispersion system being coated with an enteric polymer.

17. The method according to claim 1, wherein said composition further comprises an adjunct ingredient selected from the group consisting of fatty acid, fatty acid ester of ascorbic acid, polyenylphosphatidylcholine, and the mixture thereof.

18. The method according to claim 17, wherein said fatty acid is selected from the group consisting of lipoic acid, ascorbic acid, linoleic acid and arachidonic acid.

19. The method according to claim 17, wherein said fatty acid ester of ascorbic acid is selected from the group consisting of ascorbyl laurate, ascorbyl myristate, ascorbyl palmitate, ascorbyl stearate, and ascorbyl behenate.

20. The method according to claim 17, wherein dilinoleoylphosphatidylcholine is the most abundant phosphatidylcholine species in said polyenylphosphatidylcholine component of the composition.

21. The method according to claim 20, wherein dilinoleoylphosphatidylcholine comprises at least about 25% by weight of said polyenylphosphatidylcholine.

22. The method according to claim 20, wherein dilinoleoylphosphatidylcholine comprises at least about 40% by weight of said polyenylphosphatidylcholine.

23. The method according to claim 17, wherein said adjunct ingredient is from about 0.25% to about 0.5% by weight of the composition.

24. The method according to claim 1, wherein said pharmaceutical composition is administrated to said patient in need from one to three times a day.

25. The method according to claim 1, wherein said pharmaceutical composition is administrated to said patient in need once a day.

26. The method according to claim 1, wherein the urinary incontinence is urge incontinence, stress incontinence, mixed incontinence or overactive bladder syndrome.

* * * * *